（12) United States Patent
Sullivan

(10) Patent No.: US 9,314,469 B2
(45) Date of Patent: Apr. 19, 2016

(54) METHOD FOR TREATING NEUROCOGNITIVE DYSFUNCTION

(75) Inventor: Gregory M. Sullivan, New York, NY (US)

(73) Assignee: Tonix Pharma Holdings Limited, Hamilton (BM)

( * ) Notice: Subject to any disclaimer, the term of this patent is extended or adjusted under 35 U.S.C. 154(b) by 872 days.

(21) Appl. No.: 12/151,200

(22) Filed: May 5, 2008

(65) Prior Publication Data

US 2009/0275541 A1  Nov. 5, 2009

(51) Int. Cl.
A01N 45/00 (2006.01)
A61K 31/56 (2006.01)
A61K 31/554 (2006.01)
A61K 31/573 (2006.01)

(52) U.S. Cl.
CPC ............... A61K 31/554 (2013.01); A61K 31/56 (2013.01); A61K 31/573 (2013.01)

(58) Field of Classification Search
USPC ......................................................... 514/171
See application file for complete search history.

(56) References Cited

U.S. PATENT DOCUMENTS

| 5,405,842 | A * | 4/1995 | Silverman | ...................... | 514/171 |
| 6,599,896 | B1 | 7/2003 | Deslandes | | |
| 2005/0227961 | A1 | 10/2005 | Kucharick et al. | | |
| 2007/0010502 | A1 | 1/2007 | Keith et al. | | |

FOREIGN PATENT DOCUMENTS

EP  1 752 143  2/2007

OTHER PUBLICATIONS

Margarinos et. al. (European Journal of Pharmacology (1999) 371:113-122).*
Keenan et. al. (Neurology (1996) 47:1396-1402).*
Brown et. al. (Biol. Psychiatry (2004) 55:538-545).*
Arndt et. al. (CAS Accession # 2004467728 corresponding to Der Nervenarzt (2004) 75:904-907, see abstract in English).*
McEwen et. al. (Molecular Psychiatry (2005) 10:525-537).*
Dhikav et. al. (Medical Hypotheses (2007) 68:1300-1306).*
Reagan-Shaw et. al. (FASEB (2007) 22:659-661).*
Conrad et. al. Behav. Neurosci (1996) 110:1321-1324.*
Conrad, Chronic Stress Impairs Rdt. Spinal Memory on Y Maze and this Effect is Blocked by Tianemtne Pretreatment Bahav Neurosci 110(1006) 1321-1334.
Brown Effect of Lan Otrigene on Mood and Cognihan in Patients Receiving Chronic Endagenous Corhcosteroids, Psychosomahics 44(2003) 204-208.
Brink Tianepline: A Novel Atypical Antidepressant that May Provide New Insight Into the Biomolecular Bases of Dpression Recent Patients on CNS Drug Discovery 1(2006) 29-41.
Morris Tianeptine and its Enantromers: Effects on Spatial Memory in Rats with Medical Septum Lesions Neuropharm 41 (2001) 272-281.
Watanabe, Tianeptine Attenuates Stress-Induced Morphological Changes in Hippocampal Eur. J. Pharmacology 222(1992) 157-162.
Jaffard, Effects of Tianeptine on Spontaneous Alternation, Simple and Concurrent Spahal Discrimmation Learning and on Alcohol-Induced Alternation Deficits in Mice Bahav. Pharmacol. 2(1991) 37-46.
File, Effects of Tianeptine in Animal Models of Anxiety and on Learning and Memory, Drug Dev. Res. 23(1991) 47-56.
Boksem and Tops, "Mental fatigue: costs and benefits," Brain Res Rev 59:125-139 (2008).
Brown et al., "Hippocampal remodeling and damage by corticosteroids: implications for mood disorders," Neuropsychopharmacology, 21:474-484 (1999).
Brown et al., "The psychiatric side effects of corticosteroids," Annals of Allergy, Asthma & Immunology, 83:495-503 (1999).
Brown et al., "Effect of phenytoin onmood and declarative memory during prescription corticosteroid therapy," Biol Psychiatry, 57:543-548 (2005).
Brown et al., "Hippocampal volume, spectroscopy, cognition, and mood in patients receiving corticosteroid therapy," Biol Psychiatry 55:538-545 (2004).
Coluccia et al., "Glucocorticoid therapy-induced memory deficits: acute versus chronic effects," J Neurosci 28(13):3474-3478.
Czeh et al., "Stress-induced changes in cerebral metabolites, hippocampal volume, and cell proliferation are prevented by antidepressant treatment with tianeptine," Proc Natl Acad Sci USA 98:12796-12801 (2001).
DeLuca et al., "Functional neuroimaging of fatigue," Phys Med Rehabil Clin N Am 20:325-337 (2009).
Haas and Panula, "The role of histamine and the tuberomamillary nucleus in the nervous system," Nat Rev 4:121-130.
Knudsen, "Fundamental components of attention," Annu Rev Neurosci 30:57-78 (2007).

(Continued)

Primary Examiner — Marcos Sznaidman
(74) Attorney, Agent, or Firm — Ropes & Gray LLP; James F. Haley, Jr.; Gabriele A. Amodeo

(57) ABSTRACT

A method of treating corticosteroid-induced cognitive impairment comprises administering an effective amount of at least one compound of formula I, or pharmaceutically acceptable salts thereof, to a subject in need of such treatment. Formula I is:

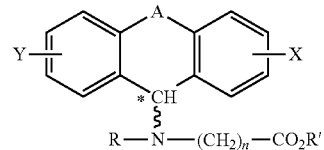

wherein: A is a bridge selected from the following radicals:
$-(CH_2)_m-$, $-CH=CH-$, $-(CH_2)_p-O-$, $-(CH_2)_p-S-$, $-(CH_2)_p-SO_2-$, $-(CH_2)_p-NR_1-$ and $-SO_2-NR_2-$, and wherein: m is an integer of from 1 to 3 inclusive; p is an integer selected from 1 and 2; $R_1$ is selected from the group consisting of hydrogen and $C_1$-$C_5$ alkyl; and $R_2$ is $C_1$-$C_5$ alkyl; X and Y are independently selected from the group consisting of hydrogen and halogen; R and R' are independently selected from the group consisting of hydrogen and $C_1$-$C_5$ alkyl; n is an integer from 1 to 12 inclusive; and * denotes an asymmetric carbon.

17 Claims, No Drawings

(56) References Cited

OTHER PUBLICATIONS

Ocon, "Caught in the thickness of brain fog: exploring the cognitive symptoms of Chronic Fatigue Syndrome," Frontiers in Physiology 4:1-8 (2013).

Pretorius, "Corticosteroids, depression and the role of serotonin," Rev Neurosci,15:109-116 (2004).

Smith and Jonides, "Storage and executive processes in the frontal lobes," Science 238:1657-1661.

Squire, "Memory and the hippocampus: a synthesis from findings with rats, monkeys, and humans," Psychol Rev 99(2):195-231 (1992).

Toon et al., "Pharmacokinetic and pharmacodynamics interaction between the antidepressant tianeptine and oxazepam at steady-state," Psychopharm 101:226-232 (1990).

* cited by examiner

METHOD FOR TREATING NEUROCOGNITIVE DYSFUNCTION

FIELD OF THE INVENTION

The present invention relates to a method for the treatment of neurocognitive side effects associated with the use of corticosteroids in the treatment of a medical condition, and related pharmaceutical compositions.

BACKGROUND OF THE INVENTION

A wide array of medical conditions are treated with systemic corticosteroids. These conditions generally involve an inflammatory process that is responsible for some of the symptoms of the condition. Among the therapeutic actions of corticosteroids at sites of inflammation are their inhibitory effects on the following immunological processes: mask cell and leukocyte degranulation, cell-mediated immune response, cellular bactericidal activity, prostaglandin and leukotriene synthesis, cytokine activity, fibrovascular proliferation, and blood vessel proliferation. Systemic corticosteroids are used to treat particular pulmonary conditions, cardiac conditions, inflammatory bowel and hepatic conditions, rheumatic conditions, collagen, vascular, and dermatological conditions, hematological conditions, neurological conditions, renal conditions, endocrine conditions, and infectious diseases, among others, the pathology of which at least in part is a result of the body's immune system response. Other uses of systemic corticosteroids include in the treatment of altitude sickness and organ transplantation.

Treatment with systemic corticosteroids is frequently associated with side effects, including cognitive dysfunction and mood instability. Thus, there is a need for agents which are effective in treating corticosteroid-induced cognitive impairment.

SUMMARY OF THE INVENTION

A method of treating corticosteroid-induced cognitive impairment comprises administering an effective amount of at least one compound of formula I, or pharmaceutically acceptable salts thereof, to a subject in need of such treatment. Formula I is:

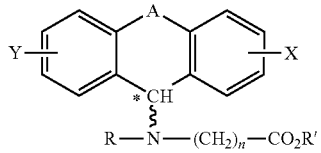

wherein: A is a bridge selected from the following radicals: —$(CH_2)_m$—, —CH=CH—, —$(CH_2)_p$—O—, —$(CH_2)_p$—S—, —$(CH_2)_p$—$SO_2$—, —$(CH_2)_p$—$NR_1$— and —$SO_2$—$NR_2$—, and wherein: m is an integer of from 1 to 3 inclusive; p is an integer selected from 1 and 2; $R_1$ is selected from the group consisting of hydrogen and $C_1$-$C_5$ alkyl; and $R_2$ is $C_1$-$C_5$ alkyl; X and Y are independently selected from the group consisting of hydrogen and halogen; R and R' are independently selected from the group consisting of hydrogen and $C_1$-$C_5$ alkyl; n is an integer from 1 to 12 inclusive; and * denotes an asymmetric carbon and the bond designated by {character pullout} indicates that the absolute conformation about the asymmetric carbon can be either (R) or (S) only when all four groups attached to the asymmetric carbon are nonequivalent. According to one embodiment, A is —$SO_2$—$NR_2$—, $R_2$ is methyl, and R and R' are hydrogen, n=6, X is a hydrogen and Y is a chlorine group and the compound is tianeptine or one of its enantiomers.

A compound of formula I may be used in the treatment of cognitive side effects that are the direct result of exogenous corticosteroids being administered as therapy for any non-central nervous system (CNS) condition. The condition may include a pulmonary condition, such as asthma, chronic obstructive pulmonary disease and pulmonary sarcoidosis; a cardiac condition, such as pericarditis; a gastrointestinal condition such as hepatitis, ulcerative colitis or Crohn's disease; a rheumatic condition, such as rheumatoid arthritis or psoriatic arthritis; a collagen-vascular or dermatological condition, such as polymyositis, polyarteritis nodosa, vasculitis, systemic dermatomyositis, eczema, cutaneous sarcoidosis, mycosis fungoides, severe seborrheic dermatitis, psoriasis, and systemic lupus erythematosus; a renal condition such as nephritic syndrome, or lupus nephritis; an endocrine condition, such as a hyperthyroid state or hypercalcemia associated with malignancy and sarcoidosis or in the prophylaxis of rejection of a transplanted organ.

Definitions

The term "alkyl", by itself or as part of another substituent means a straight, branched or cyclic chain hydrocarbon radical, including di- and multi-radicals, having the number of carbon atoms designated (ie. $C_1$-$C_5$ means one to five carbons). Alkyl groups include straight chain, branched chain or cyclic groups, with straight being preferred. Examples include: methyl, ethyl, propyl, isopropyl, butyl, isobutyl, tert-butyl, pentyl, and neopentyl.

The term "halogen" means iodine, fluorine, chlorine and bromine atoms. Preferred halogens are fluorine, chlorine and bromine atoms.

As used herein, "optically active" refers to a property whereby a material rotates the plane of plane-polarized light. A compound that is optically active is nonsuperimposable on its mirror image. As used herein, the property of nonsuperimposability of an object on its mirror image is called "chirality." The most common structural feature producing chirality is an asymmetric carbon atom; i.e., a carbon atom having four nonequivalent groups attached thereto.

As used herein, "enantiomer" refers to each of the two nonsuperimposable isomers of a pure compound that is optically active. Single enantiomers are designated according to the Cahn-Ingold-Prelog system, which is a well-known set of priority rules for ranking the four groups attached to an asymmetric carbon. See, e.g., March, Advanced Organic Chemistr. 4. th Ed., (1992), p. 109, the entire disclosure of which is herein incorporated by reference.

As used herein, "racemate" or "racemic compound" refers to a 50-50 mixture of two enantiomers such that the mixture does not rotate plane-polarized light.

By "(R)-enantiomer substantially free of the (S)-enantiomer" is meant a compound that comprises 80% or more by weight of the (R)-enantiomer, and likewise contains 20% or less by weight of the (S)-enantiomer as a contaminant. By "(S)-enantiomer substantially free of the (R)-enantiomer" is meant a compound that comprises 80% or more by weight of the (S)-enantiomer, and likewise contains 20% or less by weight of the (R)-enantiomer as a contaminant.

The term "treating" or "treatment" as used herein includes the prophylaxis of the named side effects or amelioration or elimination of the side effects once established.

DETAILED DESCRIPTION OF THE INVENTION

Compounds of formula I can be used to treat corticosteroid-induced cognitive impairment, including side effects such as memory disturbance, poor ability to concentrate, the subjective feelings of unclear thinking or being in a sedated state, and rapidly developing mental fatigue. Compounds of formula I are described as:

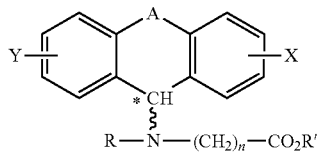

wherein: A is a bridge selected from the following radicals: —$(CH_2)_m$—, —CH=CH—, —$(CH_2)_p$—O—, —$(CH_2)_p$—S—, —$(CH_2)_p$—$SO_2$—, —$(CH_2)_p$—$NR_1$— and —$SO_2$—$NR_2$—, and wherein: m is an integer of from 1 to 3 inclusive; p is an integer selected from 1 and 2; $R_1$ is selected from the group consisting of hydrogen and $C_1$-$C_5$ alkyl; and $R_2$ is $C_1$-$C_5$ alkyl; X and Y are independently selected from the group consisting of hydrogen and halogen; R and R' are independently selected from the group consisting of hydrogen and $C_1$-$C_5$ alkyl; n is an integer from 1 to 12 inclusive; and * denotes an asymmetric carbon and the bond designated by {character pullout} indicates that the absolute conformation about the asymmetric carbon can be either (R) or (S) only when all four groups attached to the asymmetric carbon are nonequivalent, or a pharmaceutically acceptable salt thereof.

A preferred compound of formula I for use in the present methods is tianeptine, its enantiomers, its key metabolites or a pharmaceutically acceptable salt thereof. The structure of tianeptine is provided given in formula II:

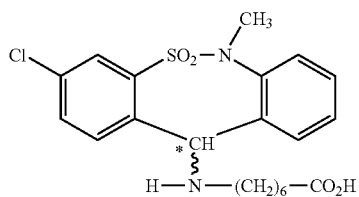

wherein: * denotes an asymmetric carbon; and the bond designated by {character pullout} indicates that the absolute conformation about the asymmetric carbon can be either (R) or (S). Tianeptine can be readily obtained by one of ordinary skill in the art, for example by the synthetic techniques described above. Tianeptine is sold commercially as Stablon®.

The compounds of formula I, in particular tianeptine, can be used to treat treatment of cognitive side effects that are the direct result of exogenous corticosteroids being administered as therapy for any non-CNS disorders in a subject who has been diagnosed with such a non-CNS disorder. As used herein, a "subject" is includes humans and non-human mammals. Non-human mammals include bovines, ovines, porcines, equines, canines, felines, and rodents (e.g., rat, mouse, guinea pig and rabbit). Preferably, the subject is a human. As used herein, non-CNS disorders include, but are not limited to, pulmonary conditions, including asthma, chronic obstructive pulmonary disease (COPD), berylliosis, aspiration pneumonitis, Loeffler's syndrome (acute pulmonary eosinophilia) and pulmonary sarcoidosis; cardiac conditions, including pericarditis; inflammatory bowel and hepatic conditions, including ulcerative colitis, Crohn's disease, regional enteritis, celiac disease, alcoholic hepatitis and subacute hepatic necrosis; rheumatic conditions, including rheumatoid arthritis, psoriatic arthritis, gouty arthritis, posttraumatic osteoarthritis, tenosynovitis, ankylosing spondylitis, Reiter's syndrome, rheumatic fever (particularly if carditis is present) and musculoskeletal injuries; collagen-vascular and dermatological conditions, including acute rheumatic carditis polymyositis, polyarteritis nodosa, vasculitis, systemic dermatomyositis, bullous dermatitis herpetiformis, severe erythema multiforme (Stevens-Johnson syndrome), exfoliative dermatitis, severe eczema, cutaneous sarcoidosis (erythema nodosum), mycosis fungoides, severe seborrheic dermatitis, erythroderma due to atopic eczema, pustular psoriasis, systemic lupus erythematosus (SLE), pyoderma gangrenosum and complicated hemangiomas; hematological conditions, including acquired (autoimmune) hemolytic anemia, idiopathic thrombocytopenic purpura (ITP), secondary thrombocytopenia, erythroblastopenia and congenital (erythroid) hypoplastic anemia; renal conditions, including nephrotic syndrome and lupus nephritis; endocrine conditions, including hyperthyroid states and hypercalcemia associated with malignancy and sarcoidosis; and infectious diseases, including *pneumocystis carinii* pneumonia (PCP), tuberculous pleurisy, infectious mononucleosis and trichinosis with myocardial involvement; and other uses of systemic corticosteroids, including altitude sickness or organ transplants (to prevent rejection of transplanted organ).

The compounds of formula I can be readily prepared by one of ordinary skill in the art. Suitable synthetic methods are found, for example, in U.S. Pat. Nos. 4,766,114, 3,758,528 and 3,821,249, all of Malen et al., and U.S. Pat. No. 6,441,165 of Blanchard et al., the entire disclosures of which are herein incorporated by reference.

Tianeptine, which has the systematic name 7-[(3-chloro-6,1'-dihydro-6-methyl-dibenzo[c,f][1,2]thiazepin-11-yl) amino]heptanoic acid S,S-dioxide, is a tricyclic anti-depressant of the dibenzothiazepine type. A sodium salt of tianeptine is currently marketed over-the-counter in Europe under the trademark Stablon®. Tianeptine is known to have psychostimulant, antidepressive, analgesic, antitussive, antihistaminic and gastric antisecretory properties. See, e.g., U.S. Pat. No. 3,758,528 of Malen et al.

Certain compounds of formula I, such as tianeptine, possess an asymmetric carbon. The position of the asymmetric carbon is denoted by an asterisk (*) in formula I; for this carbon to be considered asymmetric, each of the four groups attached to it must be nonequivalent. One skilled in the art can readily determine which compounds of formula I possess an asymmetric carbon.

Those compounds of formula I which have this asymmetric carbon can exist as both (R) and (S) enantiomers. Typically, the (R) and (S) enantiomers of a given compound of formula I exist as a racemate. In the practice of the present invention, both racemates and individual (R) or (S) enantiomers of a compound of formula I can be used to mitigate corticosteroid-induced cognitive impairment. According to certain embodiments of the invention, an (R)-enantiomer of a compound of formula I which is substantially free of the corresponding (S)-enantiomer, or an (S)-enantiomer of a compound of formula I which is substantially free of the corresponding (R)-enantiomer, is used to treat cognitive side effects that are the direct result of exogenous corticosteroids being administered as therapy for any non-CNS disorders.

To isolate the individual (R)- and (S)-enantiomers of a compound of formula I, the racemate of that compound must be resolved. This resolution can be achieved by converting a racemic compound of formula I into a pair of diastereomers, for example by covalently bonding to an optically active moiety or by salt formation with an optically active base or acid. Either method provides a molecule with a second chiral center, thus generating a pair of diastereomers. The diastereomeric pair can then be separated by conventional methods, such as crystallization or chromatography.

Racemic compounds of formula I can be separated into enantiomers without diastereomer formation, for example, by differential absorption on a chiral stationary phase of a chromatography (e.g., HPLC) column. Preparative HPLC columns suitable for diastereomer separation are commercially available with a variety of packing materials to suit a broad range of separation applications. Stationary phases suitable for resolving racemic compounds of formula I include: (i) macrocyclic glycopeptides, such as silica-bonded vancomycin which contains 18 chiral centers surrounding three pockets or cavities; (ii) chiral $\alpha_1$-acid glycoprotein; (iii) human serum albumin; and (iv) cellobiohydrolase (CBH).

In the practice of the invention, the compounds of formula I described above can take the form of a pharmaceutically-acceptable salt. The term "salts", embraces salts commonly used to form alkali metal salts and to form addition salts of free acids or free bases.

For example, pharmaceutically-acceptable acid addition salts may be prepared from an inorganic acid or from an organic acid. Suitable inorganic acids include hydrochloric, hydrobromic, hydroiodic, nitric, carbonic, sulfuric and phosphoric acid. Suitable organic acids include aliphatic, cycloaliphatic, aromatic, araliphatic, heterocyclic, carboxylic and sulfonic classes of organic acids, such as formic, acetic, propionic, succinic, glycolic, gluconic, lactic, malic, tartaric, citric, ascorbic, glucuronic, maleic, fumaric, pyruvic, aspartic, glutamic, benzoic, anthranilic, mesylic, salicylic, 4-hydroxybenzoic, phenylacetic, mandelic, embonic (pamoic), methanesulfonic, ethanesulfonic, benzenesulfonic, pantothenic, 2-hydroxyethanesulfonic, toluenesulfonic, sulfanilic, cyclohexylaminosulfonic, stearic, algenic, beta-hydroxybutyric, galactaric and galacturonic acid.

Suitable pharmaceutically acceptable base addition salts of the compounds of formula I, include metallic salts made from calcium, magnesium, potassium, sodium and zinc, or organic salts made from N,N'-dibenzylethylenediamine, chlorprocaine, choline, diethanolamine, ethylenediamine, meglumine (N-methylglucamine) and procaine. All of these salts can be prepared by conventional means from the corresponding compound of formula I by reacting, for example, the appropriate acid or base with the compound of formula I.

As used herein, an "effective amount" of a compound of formula I used to treat neurocognitive side effects associated with the use of corticosteroids in the treatment of a condition refers to the amount of the compound that prevents or alleviates one or more of the side effects associated with corticosteroid treatment. A physician can readily determine when symptoms of treatment of neurocognitive side effects associated with the use of corticosteroids in the treatment of disease are prevented or alleviated, for example through clinical observation of a subject, or through reporting of symptoms by the subject during the course of treatment.

One skilled in the art can readily determine an effective amount of a compound of formula I to be administered, by taking into account factors such as the size, weight, age and sex of the subject, the extent of disease penetration or persistence and severity of symptoms, and the route of administration. Generally, an effective amount of the compounds of formula I administered to a subject is from about 2 to about 600 mg/day, preferably from about 10 to about 400 mg/day, and more preferably about 25 to 300 mg/day. Higher or lower doses are also contemplated.

The compounds of formula I can be administered to a subject by any route, for example by enteral (e.g., oral, rectal, intranasal, etc.) and parenteral administration. Parenteral administration includes, for example, intravenous, intramuscular, intraarterial, intraperitoneal, intravaginal, intravesical (e.g., into the bladder), intradermal, topical or subcutaneous administration. Also contemplated within the scope of the invention is the instillation of the compounds of formula I into the body of the subject, for example in a controlled release formulation, with systemic or local release of the compound to occur over time or at a later time. Preferably, the compound of formula I is localized in a depot for controlled release to the circulation or to a local site such as the gastrointestinal tract.

In the practice of the present methods, compounds of formula I can be administered in the form of a pharmaceutical composition comprising at least one compound of formula I and a pharmaceutically acceptable carrier. Pharmaceutical formulations of the invention can comprise from 0.1 to 99.99 weight percent of at least one compound of formula I.

The pharmaceutical compositions of the invention can be formulated according to standard practices in the field of pharmaceutical preparations. See Alphonso Gennaro, ed., Remington's Pharmaceutical Sciences. 18th Ed., (1990) Mack Publishing Co., Easton, Pa. Suitable dosage forms can comprise, for example, tablets, capsules, solutions, parenteral solutions, troches, suppositories, or suspensions.

By "pharmaceutically acceptable carrier" is meant any diluent or excipient that is compatible with the other ingredients of the formulation, and which is not deleterious to the recipient. The pharmaceutically acceptable carrier can be selected on the basis of the desired route of administration, in accordance with standard pharmaceutical practices.

Pharmaceutical compositions of the invention for parenteral administration can take the form of an aqueous or nonaqueous solution, dispersion, suspension or emulsion. In preparing pharmaceutical compositions of the invention for parenteral administration, at least one compound of formula I can be mixed with a suitable pharmaceutically acceptable carrier such as water, oil (particularly a vegetable oil), ethanol, saline solutions (e.g., normal saline), aqueous dextrose (glucose) and related sugar solutions, glycerol, or glycols such as propylene glycol or polyethylene glycol. Pharmaceutical compositions of the invention for parenteral administration preferably contain a water-soluble salt of at least one compound of formula I. Stabilizing agents, antioxidizing agents and preservatives can also be added to the pharmaceutical compositions for parenteral administration. Suitable antioxidizing agents include sulfite, ascorbic acid, citric acid and its salts, and sodium EDTA. Suitable preservatives include benzalkonium chloride, methyl- or propyl-paraben, and chlorbutanol.

In preparing pharmaceutical compositions of the invention for oral administration, at least one compound of formula I can be combined with one or more solid or liquid inactive ingredients to form tablets, capsules, pills, powders, granules or other suitable oral dosage forms. For example, at least one compound of formula I can be combined with at least one pharmaceutically acceptable carrier such as a solvent, filler, binder, humectant, disintegrating agent, solution retarder, absorption accelerator, wetting agent absorbent or lubricating agent. In one embodiment, at least one compound of formula I is combined with carboxymethylcellulose calcium, magnesium stearate, mannitol and starch, and is formed into tablets by conventional tableting methods. In a preferred embodiment, tianeptine is formulated into a tablet comprising cellulose and a calcium salt, as described in U.S. Pat. No. 5,888,542, the entire disclosure of which is herein incorporated by reference.

Pharmaceutical compositions of the invention can also be formulated so as to provide controlled-release of at least one compound of formula I upon administration of the composition to a subject. Preferably, a controlled-release pharmaceutical composition of the invention is capable of releasing at least one compound of formula I into a subject at a desired rate, so as to maintain a substantially constant pharmacological activity for a given period of time.

Formulation of controlled-release pharmaceutical compositions of the invention is within the skill in the art. Controlled release formulations suitable for use in the present invention are described in, for example, U.S. Pat. No. 5,674,533 (liquid dosage forms), U.S. Pat. No. 5,591,767 (liquid reservoir transdermal patch), U.S. Pat. No. 5,120,548 (device comprising swellable polymers), U.S. Pat. No. 5,073,543 (ganglioside-liposome vehicle), U.S. Pat. No. 5,639,476 (stable solid formulation coated with a hydrophobic acrylic polymer), the entire disclosures of which are herein incorporated by reference.

Biodegradable microparticles can also be used to formulate controlled-release pharmaceutical compositions suitable for use in the present invention, for example as described in U.S. Pat. Nos. 5,354,566 and 5,733,566, the entire disclosures of which are herein incorporated by reference.

In one embodiment, controlled-release pharmaceutical compositions of the invention comprise at least one compound of formula I and a controlled-release component. As used herein, a "controlled-release component" is a compound such as a polymer, polymer matrix, gel, permeable membrane, liposome and/or microsphere that induces the controlled-release of the compound of formula I into the subject upon exposure to a certain physiological compound or condition. For example, the controlled-release component can be biodegradable, activated by exposure to a certain pH or temperature, by exposure to an aqueous environment, or by exposure to enzymes. An example of a controlled-release component which is activated by exposure to a certain temperature is a sol-gel. In this embodiment, at least one compound of formula I is incorporated into a sol-gel matrix that is a solid at room temperature. This sol-gel matrix is implanted into a subject having a body temperature high enough to induce gel formation of the sol-gel matrix, thereby releasing the active ingredient into the subject.

Furthermore, a compound of formula I, such as tianeptine, may be administered in combination with a systemic corticosteroid as a combination product and the pharmaceutical composition could include both compound of formula I and systemic corticosteroid. Systemic corticosteroids include cortisone, hydrocortisone, methylprednisolone, prednisolone, prednisone, triamcinolone, betamethasone, dexamethasone and the like. Corticosteroids are typically administered at about 0.1-1500 mg/day, or 0.5-30 mg/day. The total daily dosage of the compound of formula I and the corticosteroid may be administered in one, two, three, four, or more dosages. It is not necessary for the compound of formula I and the corticosteroid to be administered in the same number of daily doses.

In other embodiments, it may not be necessary for the compound of formula I and/or the corticosteroid to be administered every day or by the same route of administration. Accordingly, when administered separately, the compound of formula I and the corticosteroid are prepared in form and dosage suitable for achieving the desired treatment regimen.

The practice of the invention is illustrated by the following non-limiting example.

EXAMPLE 1

Patient was diagnosed with a medical condition known as pulmonary sarcoidosis in which immune cells (lymphocytes and macrophages) are abnormally activated and accumulate in the lung, progressively destroying the architecture and functional capacity of lung tissue. Treatment is necessary to prevent progression of the disease and loss of more pulmonary functional capacity. Standard treatment is with systemic corticosteroids due to the capacity of corticosteroids for suppressing immune function. Patient was started on prednisone 40 mg by mouth each morning, with a plan to taper the dose by 5 mg every two weeks until at 25 mg a day. After three months the level of response to corticosteroids would be assessed by repeat pulmonary function tests and chest x-ray. If the disease process was responsive to corticosteroids, the treatment would be continued to finish a full year on about 25 mg a day.

Over the first several days on prednisone, patient experienced severe memory disturbance, poor ability to focus or concentrate, and a constant "foggy" feeling. The memory disturbance was profound and sharply contrasted with patient's normal memory function. The "foggy" feeling was present all day long, and was similar to the feeling of having taken a sedating antihistamine like diphenhydramine (Benadryl). Patient found he could only concentrate with much effort, with rapidly developing mental fatigue preventing sustained efforts. Examples of memory impairment resulting from the prednisone were much like some of the memory disturbance seen in Alzheimer's dementia in which there is impairment in the process of consolidation of short term memories into long term memories, a process known to depend on intact hippocampal function.

Patient began tianeptine (Stablon) at 12.5 mg, one pill in the morning. Four days later, patient increased the dose to 12.5 mg twice a day, finally, two days after the prior increase, patient increased the dose to 25 mg each morning and 12.5 mg each evening. In the first several days taking tianeptine, patient noted the "foggy" feeling had gone away. Patient's ability to concentrate also appeared to normalize. Episodic memory also significantly improved.

Although beginning tianeptine correlated with the rapid improvement in cognitive function, it was uncertain whether the tianeptine was responsible for the improvement.

There was the alternate possibility that patient was simply adjusting to the corticosteroids, with reduction in the cognitive side effects manifesting over the first several weeks after beginning corticosteroids. Nonetheless, patient continued to take the tianeptine. Also, it seemed possible that prednisone at 40 mg a day had been producing worse side effects than the lower doses of 35 mg, 30 mg, and 25 mg a day patient had tapered down to after starting the tianeptine. Follow-up pulmonary function tests a month later indicated improvement and therefore prednisone was continued at 25 mg a day.

Patient stopped tianeptine treatment two months later, tapering the dose over three days. Within about 2-3 days after the final dose of tianeptine, patient experienced the gradual emergence of the same cognitive side effects of the corticosteroids that patient had been experiencing in before initial tianeptine treatment including poor memory, extreme difficulty concentrating and sustaining mental effort, and the general "foggy" feeling once again pervading. This continued up for two weeks when patient restarted tianeptine treatment. Within 24 hours of restarting tianeptine, patient noted definite improvement. After three days, patient's cognitive function had pretty much returned to normal baseline. Patient has continued on tianeptine 25 mg each morning and 12.5 mg each evening since then. This episode of reemergence of cognitive dysfunction off tianeptine and relief of cognitive dysfunction once back on tianeptine proved that there was indeed a large effect of the tianeptine in mitigating the side effects of the corticosteroids and that this function of tianeptine occurred over a short time frame (24-72 hours) after initiation of treatment.

All references cited herein are incorporated by reference. The present invention may be embodied in other specific forms without departing from the spirit or essential attributes thereof and, accordingly, reference should be made to the appended claims, rather than to the foregoing specification, as indication the scope of the invention.

What is claimed is:

1. A method of treating a cognitive impairment associated with corticosteroid treatment as a result of a condition in a human in need of such treatment, comprising administering to the human an effective amount of at least one compound of formula I

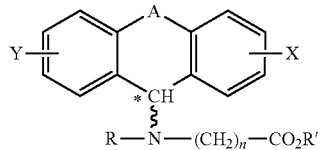

wherein: A is a bridge selected from the following radicals: —(CH$_2$)$_m$—, —CH=CH—, —(CH$_2$)$_p$—O—, —(CH$_2$)$_p$—S—, —(CH$_2$)$_p$—SO$_2$—, —(CH$_2$)$_p$—NR$_1$— and —SO$_2$—NR$_2$—, and wherein: m is an integer of from 1 to 3 inclusive; p is an integer selected from 1 and 2; R$_1$ is selected from the group consisting of hydrogen and C$_1$-C$_5$ alkyl; and R$_2$ is C$_1$-C$_5$ alkyl; X and Y are independently selected from the group consisting of hydrogen and halogen; R and R' are independently selected from the group consisting of hydrogen and C$_1$-C$_5$ alkyl; n is an integer from 1 to 12 inclusive; and * denotes an asymmetric carbon and the bond designated by {character pullout} indicates that the absolute conformation about the asymmetric carbon can be either (R) or (S) only when all four groups attached to the asymmetric carbon are nonequivalent, or a pharmaceutically acceptable salt thereof, and wherein said cognitive impairment is selected from the group consisting of a foggy feeling, a poor ability to concentrate, unclear thinking, being in a sedated state, and a rapidly developing mental fatigue.

2. The method according to claim 1, wherein A is —SO$_2$—NR$_2$—.

3. The method according to claim 2, wherein R and R' are hydrogen.

4. The method of claim 1, wherein the compound of formula I is tianeptine or a pharmaceutically acceptable salt thereof.

5. The method of claim 4, wherein the compound is (R)-tianeptine, substantially free of the corresponding (S)-enantiomer.

6. The method of claim 4, wherein the compound is (S)-tianeptine, substantially free of the corresponding (R)-enantiomer.

7. The method of claim 1, wherein the effective amount of the at least one compound of formula I administered to the human is from about 2 to about 600 mg/day.

8. The method of claim 1, wherein the effective amount of the at least one compound of formula I administered to the human is from about 10 to about 400 mg/day.

9. The method of claim 1, wherein the effective amount of the at least one compound of formula I administered to the human is about 25 to about 300 mg/day.

10. The method of claim 1, wherein the at least one compound of formula I is administered to the subject as a pharmaceutical composition.

11. The method of claim 10, wherein the condition is a pulmonary condition.

12. The method of claim 11, wherein the pulmonary condition is selected from the group consisting of asthma, chronic obstructive pulmonary disease and pulmonary sarcoidosis.

13. The method of claim 10, wherein the condition is selected from the group consisting of a cardiac condition, a gastrointestinal condition, a rheumatic condition, a collagen-vascular or dermatological condition, a renal condition, an endocrine condition.

14. The method of claim 13, wherein the condition is pericarditis, hepatitis, ulcerative colitis or Crohn's disease, rheumatoid arthritis or psoriatic arthritis, polymyositis, polyarteritis nodosa, vasculitis, systemic dermatomyositis, eczema, cutaneous sarcoidosis, mycosis fungoides, severe seborrheic dermatitis, psoriasis, and systemic lupus erythematosus, nephritic syndrome, or lupus nephritis, a hyperthyroid state or hypercalcemia associated with malignancy and sarcoidosis.

15. The method of claim 10, wherein the condition is the prophylaxis of the rejection of a transplanted organ.

16. The method of claim 1, wherein the compound of formula I is administered with a systemic corticosteroid.

17. The method of claim 16, wherein the systemic corticosteroid is prednisone.

* * * * *